US006762053B2

(12) United States Patent
Gardner et al.

(10) Patent No.: US 6,762,053 B2
(45) Date of Patent: Jul. 13, 2004

(54) MAMMALIAN GAMETE AND EMBRYO CULTURE MEDIA AND CULTURE MEDIA SUPPLEMENTS

(75) Inventors: David K. Gardner, Highlands Ranch, CO (US); Michelle T. Lane, Highlands Ranch, CO (US)

(73) Assignee: Vitrolife, Inc., Englewood, CO (US)

( * ) Notice: Subject to any disclaimer, the term of this patent is extended or adjusted under 35 U.S.C. 154(b) by 0 days.

(21) Appl. No.: 09/877,395

(22) Filed: Jun. 8, 2001

(65) Prior Publication Data

US 2002/0042132 A1 Apr. 11, 2002

Related U.S. Application Data

(60) Provisional application No. 60/212,232, filed on Jun. 16, 2000, and provisional application No. 60/210,649, filed on Jun. 9, 2000.

(51) Int. Cl.[7] .................................................. C12N 5/00
(52) U.S. Cl. .................... 435/407; 435/325; 435/404
(58) Field of Search ................................. 435/325, 404, 435/407, 366, 383, 388, 69, 172.3, 252.3, 254.2, 320.1; 514/8, 12; 530/267, 364

(56) References Cited

U.S. PATENT DOCUMENTS

| 5,612,196 | A | * | 3/1997 | Becquart et al. ........... 435/69.6 |
| 6,140,121 | A | * | 10/2000 | Ellington et al. ........... 435/374 |
| 6,153,582 | A | * | 11/2000 | Skelnik ....................... 514/12 |

FOREIGN PATENT DOCUMENTS

| EP | 0 947 581 A1 | 8/1997 |
| WO | WO 00/32140 | 6/2000 |

OTHER PUBLICATIONS

Kjems et al. Isolation of Hyaluronic acid from cultures of streptococci in a chemically defined medium. Acta Pat. Microbiol. Scand. Sect. B 84:162–164, 1976.*
Gene Characterization Kits, Stratagene Catalog, 1998, pp. 39.*
T. Miyano et al., Effects of Hyaluronic Acid on The Development of 1– and 2–Cell Procine Embryos To The Blastocyst Stage In Vitro, Theriogenology, 41: pp. 1299–1305, pp. 1994.*
Gardner, David K., et al., "Culture of viable human blastocysts in defined sequential serum–free media," Human Reproduction (Oxford), vol. 13, Suppl. 3, Jun. 1998, pp. 148–159; published by European Society for Human Reproduction and Embryology.

Keenan, J., et al., "Recombinant human albumin in cell culture: Evaluation of growth–promoting potential for NRK and SCC–9 cells in vitro," Cytotechnology, vol. 24, No. 3, 1997, pp. 243–252; published by Kluwer Academic Publishers.

Kane, Michel T., et al., "Protein–Free Culture Medium Containing Polyvinylalcohol, Vitamins, and Amino Acids Supports Development of Eight–Cell Hamster Embryos to Hatching Blastocysts," *The Journal of Experimental Zoology*, vol. 247, pp. 183–187, 1988.

McKiernan, Susan H., et al., "Different Lots of Bovine Serum Albumin Inhibit or Stimulate in Vitro Development of Hamster Embryos," *In Vitro Cell Div. Biol.*, vol. 28A, pp. 154–156, Mar. 1992.

Batt, P.A., et al., "Oxygen Concentration and Protein Source Affect the Development of Preimplanation Goat Embryos *In Vitro*," *Reprod. Fertil. Dev.*, vol. 3, pp. 601–607, 1991.

Kane, Michael T., "Minimal Nutrient Requirements for Culture of One–Cell Rabbit Embryos," *Biology of Reproduction*, vol. 37, pp. 775–778, 1987.

Gray, C. W., et al., "Purification of an Embryotrophic Factor From Commercial Bovine Serum Albumin and Its IDentification as Citrate," *J. Reprod. Fert.*, vol. 94, pp. 471–480, 1992.

Farrar, N.C., et al., "Effects of Serum or Fatty Acid Supplementation of Synthetic Oviduct Fluid Medium on Development of Bovine Embryos *In Vitro*," Abstract from a presentation at a meeting of the British Society of Animal Science, Sep. 1999.

* cited by examiner

*Primary Examiner*—Dave T. Nguyen
*Assistant Examiner*—Jon Eric Angell
(74) *Attorney, Agent, or Firm*—Foley & Lardner

(57) ABSTRACT

The present invention provides a supplement and a culture media useful for culturing mammalian gametes and embryonic tissue. The culture media comprises at least one of recombinant human albumin, fermented hyaluronan, and citrate. Because the constituents are produced from non-conventional sources, the culture medium is free from contaminants such as viruses, prions and endotoxins. Additionally, because the medium is completely defined, the medium is not subject to variations which can impair the development of mammalian cells and prevent meaningful comparisons of empirical studies.

19 Claims, No Drawings

MAMMALIAN GAMETE AND EMBRYO CULTURE MEDIA AND CULTURE MEDIA SUPPLEMENTS

This application claims priority from Provisional Application No. 60/210,649 filed Jun. 9, 2000 and Provisional Application No. 60/212,232 flied Jun. 16, 2000.

FIELD OF THE INVENTION

The present invention relates to culture media which provide useful environments for cellular development. More particularly this invention relates to defined culture media supplement containing constituents produced from non-traditional sources that, when added to culture media, avoid the problems of prior culture media.

BACKGROUND OF THE INVENTION

For years media supplements for culturing mammalian embryonic cells have been derived from animal fluids, and in particular blood serum. While serum based media supplements have been somewhat effective for culturing certain types of cells and tissues, these media supplements have been found to be undesirable. One of the main reasons that these serum based media supplements are unattractive candidates for culturing cells is because of the possibility that the resulting media will contaminated with impurities, toxins, and infective agents found in the fluid from which the media is derived. Additionally, because the animals from which the blood is collected are different and live in differing environments, the fluids produced by these animals have different components at differing concentrations. One important aspect of serum based medium that has been recognized is the requirement of macromolecules in the medium. In an attempt to mimic serum based products, researchers have attempted to add synthetic macromolecules, such as polyvinyl alcohol, to replace the macromolecules in the serum, such as albumin. However, because serum is largely undefined chemically, removing the serum from culture media and attempting to replace only the larger molecules has produced culture media which are less than ideal or ineffective for many purposes because the media are missing essential components.

Accordingly, there is a need for culture media supplements which are as effective as culture media supplements based on blood products while at the same eliminating potential sources of contamination. Additionally there is a need for standardized culture media.

SUMMARY OF THE INVENTION

The present invention describes a novel, physiologically based completely defined supplement to culture media for mammalian embryonic cells and gametes. This medium supplement may be used with in vitro fertilization media, embryo transfer media and embryo cryopreservation media for the mammalian preimplantation embryo, as well as a supplement to media for the development of embryonic stem cells, or any other similar media well known in the art. This supplement contains recombinant human albumin (rHA), fermented hyaluronan (HYN) and/or citrate, and combinations thereof. Addition of this supplement to the culture medium results in equivalent development compared to media supplemented with serum albumin purified from blood.

DETAILED DESCRIPTION OF THE INVENTION

The supplement may comprise recombinant human albumin (rHA) at any appropriate concentrations for the media in which it is to be used. As further described herein, the use of rHA rather than naturally occurring human serum albumin (HSA) has numerous advantages.

Typically, when the supplement comprises rHA, the supplement comprises between about 0.1 mg/ml to about 20.0 mg/ml of rHA based on the total volume of the medium to which the supplement is added. In one embodiment, about 0.5 mg/ml to about 5.0 mg/ml of rHA is added based on the total volume of the medium.

The efficacy of the supplement can be enhanced by adding fermented hyaluronan (HYN) to the supplement. The addition of the fermented HYN to the media supplement demonstrates positive results.

The phrase "increases the viability of gametes or embryonic cells" as used herein is defined as including the increased development of the embryos to the blastocyst stage in the culture, the ability to hatch from the zona pellucida is increased in vitro, and/or an increase in the overall viability of the embryo in embryo cultures when embryos are cultured in a medium containing the supplement of the present invention as compared to being cultured in the same medium without the supplement.

Furthermore, the addition of fermented HYN to the appropriate medium significantly affects the ability of the blastocysts to survive freezing. The use of fermented HYN has several advantages over the use of HYN from a naturally occurring warm blooded vertebrate source such as purified from rooster comb or umbilical cord. By utilizing fermented HYN rather than HYN from a warm blooded vertebrate source, the ability to control the safety and stability of the HYN from different sources and batches is greatly increased.

When present, the amount of fermented HYN will generally be at concentrations between about 0.1 mg/ml to about 5.0 mg/ml based on the total volume of the medium. In one embodiment the fermented HYN will be added to the medium at concentrations between about 0.125 mg/ml to about 1.0 mg/ml based on the total volume of the medium.

The supplement can be further augmented by the addition of citrate. In one embodiment, citrate and rHA are both added to the medium supplement, as it has been surprisingly and unexpectedly discovered that the addition of citrate to a medium supplement containing rHA allows the rHA to closely duplicate the properties of HSA or bovine serum albumin (BSA). The addition of the citrate has a further enhancing effect on the development of the cultured cellular material. Any citrate used for media that is well known in the art may be used, including, but not limited to, choline citrate, calcium citrate, citric acid, sodium citrate, and combinations thereof. In one embodiment, sodium citrate is used. The citrate is generally added at concentrations between about 0.1 mM and about 5.0 mM, based on the total volume of the medium. In one embodiment, the citrate is added at concentrations between about 0.1 mM and about 1.0 mM, based on the total volume of the medium.

The medium supplement of the present invention comprises rHA, fermented HYN and/or citrate in any useful combination. In one embodiment, the medium supplement, and the medium to which the medium supplement is added, is free from non-recombinant macromolecules or macromolecules purified from an animal source. In another embodiment, the medium supplement, and the medium to which the medium supplement is added, is free of non-recombinant HSA and/or non-fermented HYN.

This invention is directed to the medium supplement described above, media containing the medium supplement, a method of making the medium supplement, kits containing the medium supplement, and a method of growing embryonic material employing the medium supplement described herein.

The present invention includes a method of growing cellular material, in one embodiment embryos, employing the medium supplement described herein such that they can be included in medium at the start of culture, or can be added in a fed-batch or in a continuous manner. Moreover, the components of the medium supplement may be added together, or separately, at different stages of the media production.

This supplement can be added to any appropriate mammalian cellular material culture media well known in the art, including but not limited to, embryo culture media, embryo transfer media and embryo cryopreservation media (to include both freezing and vitrification procedures) for embryos from any mammalian species, and stem cell media. Any media that can support embryo or cell development could be used, which includes, by way of example only, bicarbonate buffered medium, Hepes-buffered or MOPS buffered medium or phosphate buffered saline. Examples of media are G1.2/G2.2, KSOM/KSOMaa, M16, SOF/SOFaa, MTF, P1, Earle's, Hams F-10, M2, Hepes-G1.2, PBS and/or Whitten's. (Gardner and Lane, 1999; Embryo Culture Systems; Handbook of In Vitro Fertilization, CRC Press, Editors: Trounson A O and Gardner D K, $2^{nd}$ edition, Boca Raton, pp 205–264.)

The production of rHA is well known in the art. In one embodiment, rHA is obtained from genetically modified yeast which produce a human albumin protein. One such methodology for the production of rHA from yeast is taught in U.S. Pat. No. 5,612,197.

Fermented hyaluronan (HYN) is obtained by any process well known in the art. One such process is the continuous bacterial fermentation of Streptococcus equi. Hyaluronan is a naturally occurring polymer of repeated disaccharide units of N-acetylglucosamine and D-glucuronic acid. It is widely distributed throughout the body. Typically, the molecular weight of the fermented HYN is $2.3 \times 10^6$ kD. The production of HYN from Streptococcus is well known in the art, and any well known process can be used, including those disclosed in Cifonelli J A, Dorfman A. The biosynthesis of hyaluronic acid by group A Streptococcus: The uridine nucleotides of groups A Streptococcus. J. Biological Chemistry 1957; 228: 547–557; Kjems E, Lebech K. Isolation of hyaluronic acid from cultures of streptococci in a chemically defined medium. Acta Path. Microbiol. Scand. 1976 (Sect. B); 84: 162–164; and Markovitz A, et al. The biosynthesis of hyaluronic acid by group A Streptococcus. J. Biological Chemistry 1959; 234(9): 2343–2350.

Other compounds may be added to the medium supplement of the present invention. These include growth factors, as mammalian embryos and cells typically have many receptors for growth factors and the addition of such growth factors may increase the growth rate of the cultured material. Such growth factors include, but are not limited to, Insulin, typically in amounts of 0.1–100 ng/ml; IGF II, typically in amounts of 0.1–100 ng/ml; EGF, typically in amounts of 0.1–100 ng/ml; LIF, typically in amounts of 5–1000 U/ml; PAF, typically in amounts of 0.1–500 $\mu$M; and combinations thereof. All amounts are based on the total volume of the media to which the medium supplement is added.

Medium supplement can be prepared in 2 ways, either as a separate medium supplement that is added to the media after media preparation, or the ingredients of the medium supplement can be added directly to the culture media during media preparation.

By way of example only, the medium supplement may be prepared on its own as follows. Medium supplement rHA may be made into a stock solution by adding either water, saline or medium to make a concentrated stock solution of between 50–500 mg/ml, usually 250 mg/ml. Alternatively, the solution can be obtained as a 250 mg/ml stock solution. Fermented HYN is reconstituted in water, saline or medium, to make a concentrated stock solution of between 10–500 mg/ml, usually 500 mg/ml. This is achieved by adding the water, saline or medium to a flask and adding the desired amount of HYN to the solution. The HYN is then dissolved by rigorous shaking or mixing using a stir bar. For a 500 mg/ml solution, 500 mg of HYN can be added to 1 ml of solution. Citrate is prepared as a stock solution by adding either water, saline or medium to make a concentrated stock solution of between 5–500 mM, usually 500 mM. For a 500 mM stock solution, 0.9605 g of citric acid is added to 10 ml of solution. The rHA, fermented HYN and citrate stocks are added together to make a single supplement solution that is added to the final medium as a 100×times concentrated stock. For 10 ml of medium, 100 $\mu$l of the supplement is added.

rHA can be added directly to the culture medium as either a powder or as a stock solution. The following embodiment is presented by way of example only. The stock solution may added as 100 $\mu$l of 250 mg/ml stock to 9.9 mls of medium. Fermented HYN may be added directly to the culture medium as either a powder or as a stock solution. As a powder, 1.25 mg of HYN may be added to 10 ml of medium. Alternatively, a 125 $\mu$l of a 1% stock solution may be added to 9.9 ml of medium. Citrate may be added directly to the culture medium as either a powder or as a stock solution. As a powder, 9.6 mg may be added to 100 mls of medium, or alternatively, 100 $\mu$l of a 50 mM stock may be added to 9.9 ml of medium.

All patents and publications cited herein are hereby incorporated by reference.

All ranges recited herein include all combinations and subcombinations included within that range limits; therefore, a range from "about 0.1 mg/ml to about 20.0 mg/mil" would include ranges from about 0.125 mg/ml to about 11.5 mg/ml, about 1.0 mg/ml to about 15.0 mg/ml, etc.

The medium supplement of the present invention solves several problems that persist in the art of culturing mammalian cells, tissues, embryos and other related cellular material. One problem with current media is that the cultured mammalian cellular material, particularly embryos, may become contaminated by contaminants such as prions and/or endotoxins found within macromolecular blood products such as human albumin. An advantage of the supplement of the present invention is that it eliminates the potential contamination associated with the use of blood products in media for culturing embryo and other mammalian cellular materials.

Another problem with current media is the difficulty in standardizing such media when using blood products such as serum albumin or other naturally occurring materials. Furthermore, the present invention makes it easier to purify the final cultured product, when the naturally occurring variations and contaminants within the blood products in the media are eliminated.

The present invention eliminates the inherent variation involved when using a biological protein which is often contaminated with other molecules and which differs significantly between different preparations and also between batches within the same preparation. Therefore, the use of recombinant molecules such as rHA enables the formulation of physiological media to be prepared in a standardized fashion. These preparations are endotoxin free, free of prions and are more physiologically compatible than media which are currently used. Current media contain other synthetic macromolecules, such as polyvinyl alcohol or polyvinyl pyrrolidone, which are unable to perform essential physiological functions, such as bind growth factors, and therefore the use of these media result in inferior development of mammalian cellular material.

The invention will be better understood from the Examples which follow. However, one skilled in the art will readily appreciate that the specific compositions, methods and results discussed are merely illustrative of the invention and no limitations on the invention are implied.

EXAMPLES

Example 1

Media G1.2/G2.2 were prepared from concentrated stock solutions as shown below in Table 1. rHA was added as a 250 mg/ml stock solution of 200 µl to 9.8 mls of media. Initial experiments have investigated replacing albumin purified from blood with the rHA for outbred mouse embryo development in culture. Fertilized eggs were cultured for 4 days in one of 3 different concentrations of rHA. Embryos were cultured at 37° C. in 6% $CO_2$:5% $O_2$:89% $N_2$ in an embryo incubation volume of 10 embryos:20 µl of medium. Embryos were cultured in medium G 1.2 for 48 h followed by 48 h of culture in medium G 2.2. The negative control treatment was no protein, the positive control treatment was 5 mg/ml HSA (blood product). The results are shown below in Table 2.

TABLE 1

| Stock | Expires | Components | G1.2 (g/L) | G2.2 (g/L) | FG1 (g/L) |
|---|---|---|---|---|---|
| A ×10 conc | 3 months | NaCl | 5.26 | 5.26 | 5.844 |
| | | KCl | 0.41 | 0.41 | 0.41 |
| | | $NaH_2PO_4$—$H_2O$ | 0.035 | 0.035 | 0.078 |
| | | $MgSO_4$—$7H_2O$ | 0.246 | 0.246 | 0.246 |
| | | Na Lactate | 1.17 | 0.66 | 0.58 |
| | | Glucose | 0.09 | 0.568 | 0.567 |
| | | Penicillin | 0.06 | 0.06 | 0.06 |
| B ×10 conc | 1 week | $NaHCO_3$ | 2.101 | 2.101 | 2.1 |
| | | Phenol Red | 0.001 | 0.001 | 0.001 |
| C ×100 conc | 2 weeks | Pyruvic Acid | 0.0352 | 0.011 | 0.0352 |
| D ×100 conc | 1 month | $CaCl_2$—$H_2O$ | 0.265 | 0.265 | 0.265 |
| G ×100 conc | 3 months | alanyl-Glutamine | 0.108 | 0.217 | — |

TABLE 1-continued

| Stock | Expires | Components | G1.2 (g/L) | G2.2 (g/L) | FG1 (g/L) |
|---|---|---|---|---|---|
| T ×100 conc | 3 months | Taurine | 0.0125 | — | 0.0125 |
| ED | 1 month | EDTA | 0.029 | — | — |
| | | NaOH solution | 0.4 | | |
| N ×100 soln | | Non-Essential Amino Acids | 10 ml | 10 ml | 10 ml |
| E ×50 soln | | Essential Amino Acids | — | 20 ml | — |
| V ×100 soln | | Vitamins | — | 10 mls | 10 ml |

Stock A and B

1. Weigh out individual components into a 100 ml flask.
2. Add 50 ml of $H_2O$ (either Extreme $H_2O$ or Biowittaker).
3. Mix well until all components are dissolved.
4. Add a further 50 ml of $H_2O$.
5. Mix well.
6. Filter through 0.2 µm filter.
7. Store at 4 degrees Celsius.

Stock C-T

1. Weigh component into a 10 ml tube.
2. Add 10 ml of $H_2O$ (either Extreme $H_2O$ or Biowittaker).
3. Mix well until dissolved.
4. Filter through 0.2 µm filter.
5. Store at 4 degrees Celsius.

Embryo Culture Media Preparation—Part I

Stock EDTA

1. Weigh 0.029 g of EDTA into a 10 ml tube.
2. Weigh 0.4 g of NaOH into a separate 10 ml tube.
3. Add 10 ml of $H_2O$ (either Extreme $H_2O$ or Biowittaker) to NaOH and mix until dissolved.
4. Add 220 µl of NaOH solution to EDTA.
5. Mix until dissolved.
6. Add 9.8 ml of $H_2O$ to the EDTA.
7. Add 90 ml of $H_2O$ to a 100 ml flask.
8. Add 10 ml of EDTA solution to the 90 ml of H20.
9. Filter through 0.2 µm filter.
10. Store at 4 degrees Celsius.

TABLE 2

| rHA mg/ml | Blastocyst | Hatching | Cell Number | ICM Number | TE Number | % ICM/Total |
|---|---|---|---|---|---|---|
| 0 | 76.7 | 31.7 | $60.8 \pm 2.2^a$ | $13.8 \pm 0.7^a$ | $47.1 \pm 2.0^a$ | $23.0 \pm 0.9$ |
| 1.25 | 70.7 | 46.6 | $72.6 \pm 2.2^{bc}$ | $17.7 \pm 0.6^b$ | $56.4 \pm 1.9^{bc}$ | $24.0 \pm 0.6$ |
| 2.5 | 75 | 39.3 | $78.1 \pm 2.5^b$ | $18.4 \pm 0.5^b$ | $58.4 \pm 2.1^b$ | $24.2 \pm 0.5$ |
| 5 | 76.8 | 37.5 | $65.9 \pm 2.7^{ac}$ | $16.3 \pm 0.7^b$ | $49.6 \pm 2.4^{ac}$ | $25.2 \pm 0.7$ |
| HSA 5 mg/ml | 72.6 | 38.7 | $74.3 \pm 2.4^{bc}$ | $17.2 \pm 0.7^b$ | $56.2 \pm 2.0^{bc}$ | $23.6 \pm 0.6$ |

*Different superscripts are significantly different, $P < 0.05$.

rHA was able to replace HSA for embryo development in culture for at least concentrations of 1.25 to 2.5 mg/ml.

Example 2

Media G1.2/G2.2 were prepared from concentrated stock solutions as taught in Example 1. Fermented HYN was added from a ×100 stock solution of 100 μl to 10 mls of media.

Initial experiments investigated replacing albumin purified from blood with HYN for outbred mouse embryo development in culture. Fertilized eggs were cultured for 4 days in one of 4 different concentrations of HYN. Embryos were cultured at 37° C. in 6% $CO_2$:5% $O_2$: 89% $N_2$ in an embryo incubation volume of 10 embryos:20 μl of medium. Embryos were cultured in medium G1.2 for 48 h followed by 48 h of culture in medium G2.2. The negative control treatment was no protein. The results are shown below in Table 3.

TABLE 3

| HYN (mg/ml) | Blastocyst | Hatching | Cell Number | ICM Number | TE Number | % ICM/Total |
|---|---|---|---|---|---|---|
| 0 | $82.4^a$ | $38.3^a$ | $67.3 \pm 2.8^a$ | $16.1 \pm 0.7^a$ | $50.3 \pm 2.3^a$ | $24.6 \pm 0.8^a$ |
| 0.125 | $88.6^a$ | $57.1b^c$ | $79.6 \pm 1.9^{bc}$ | $21.2 \pm 0.8^{bc}$ | $58.7 \pm 1.5^{bc}$ | $26.5 \pm 0.6^{ac}$ |
| 0.25 | $94.5^a$ | $72.7^c$ | $74.9 \pm 3.4^{bc}$ | $21.8 \pm 1.2^{bc}$ | $51.9 \pm 2.8^{ac}$ | $29.7 \pm 0.8^{bc}$ |
| 0.5 | $100^a$ | $50^b$ | $64.2 \pm 1.9^{ac}$ | $18.0 \pm 0.7^{ac}$ | $46.7 \pm 2.0^a$ | $28.3 \pm 1.1^{bc}$ |
| 1 | $61.8^b$ | $23.5^a$ | $62.0 \pm 2.7^{ac}$ | $17.5 \pm 0.8^{ac}$ | $49.1 \pm 2.5^a$ | $26.4 \pm 0.9^{ac}$ |

*Different superscripts are significantly different, $P < 0.05$.

Fermented HYN at least of concentrations from 0.125 to 0.5 mg/ml stimulated mouse embryo development.

Example 3

Media G1.2/G2.2 were prepared from concentrated stock solutions as taught in Example 1. rHA was added as a 250 mg/ml stock solution of 200 μl to 9.8 mls of media, fermented HYN was added from a ×100 stock solution of 100 μl to 10 mls of media. Subsequent experiments investigated replacing albumin purified from blood with rHA together with fermented HYN for outbred mouse embryo development in culture. Fertilized eggs were cultured for 4 days. Embryos were cultured at 37° C. in 6% $CO_2$:5% $O_2$:89% $N_2$ in an embryo incubation volume of 10 embryos:20 μl of medium. Embryos were cultured in medium G 1.2 for 48 h followed by 48 h of culture in medium G 2.2. The results are shown below in Table 4.

TABLE 4

| Treatment | Cell Number | ICM Number | TN Number | % ICM/Total |
|---|---|---|---|---|
| 5 mg/ml HSA | $73.3 \pm 1.7$ | $17.8 \pm 0.6$ | $55.5 \pm 1.3$ | $24.3 \pm 0.5$ |
| 1.25 mg/ml rHA + 0.125 mg/ml HYN | $71.8 \pm 1.6$ | $18.6 \pm 0.5$ | $53.2 \pm 1.3$ | $26.0 \pm 0.5$* |

*Significantly different from the HSA (blood product).

Culture with rHA and fermented HYN together significantly increase the development of the inner cell mass cells (ICM). Since ICM development is linearly related to ability to develop into a viable fetus, an increase in % ICM is likely to mean an increase in viability.

Example 4

Media G1.2/G2.2 were prepared from concentrated stock solutions as taught in Example 1. rHA was added as a 250 mg/ml stock solution of 200 μl to 9.8 mls of media, fermented HYN was added from a ×100 stock solution of 100 μl to 10 mls of media. Subsequent experiments investigated replacing albumin purified from blood with rHA together with fermented HYN for outbred mouse embryo development after transfer to recipient mice. Fertilized eggs were cultured for 4 days and then transferred at the blastocyst stage to recipient females. Embryos were cultured at 37° C. in 6% $CO_2$:5% $O_2$:89% $N_2$ in an embryo incubation volume of 10 embryos:20 μl of medium. Embryos were cultured in medium G1.2 for 48 h followed by 48 h of culture in medium G2.2. The results are shown below in Table 5.

TABLE 5

| | Implantation rate (%) | Fetal development (%) | Fetus/implantation site (%) | Weight (mg) |
|---|---|---|---|---|
| HSA | 63.3 | 43.3 | 68.4 | 208 |
| rHA and HYN | 65.0 | 46.7 | 71.8 | 207 |

Culture with rHA together with fermented HYN resulted in equivalent fetal development to those embryos cultured in medium supplemented with HSA (blood product).

Example 5

Media G1.2/62.2 were prepared from concentrated stock as taught in Example 1. rHA was added as a 250 mg/ml stock solution of 200 μl to 9.8 mls of media, fermented HYN was added from a ×100 stock solution of 100 μl to 10 mls of media and citrate was added from a ×100 stock solution of 100 μl to 10 mls of media. Experiments were performed to determine whether the further supplementation of rHA and fermented HYN together with citrate increased mouse embryo development in culture. Embryos were cultured from the fertilized egg for 48 h with rHA and HYN in the presence or absence of citrate. Embryos were cultured at 37° C. in 6% $CO_2$:5% $O_2$:89% $N_2$ in an embryo incubation volume of 10 embryos:20 μl of medium. Embryos were cultured in medium G1.2 for 48 h. The results are shown below in Table 6.

TABLE 6

|  | Day 3 mean cell number | % 8 cell | % compacted |
|---|---|---|---|
| no citrate | 6.33 ± 0.17 | 69.7 | 7.3 |
| citrate | 7.21 ± 0.13* | 81.1* | 12.2* |

*Significantly different from medium lacking citrate, P < 0.05.

The addition of citrate to medium containing rHA and fermented HYN resulted in a significant increase in embryo development.

Example 6

Media G1.2/G2.2 were prepared from concentrated stock solutions as taught in Example 1. rHA was added as a 250 mg/ml stock solution of 200 μl to 9.8 mls of media, fermented HYN was added from a ×100 stock solution of 100 μl to 10 mls of media and citrate was added from a ×100 stock solution of 100 μl to 10 mls of media. Experiments were performed to determine whether the further supplementation of rHA and fermented HYN together with citrate increased mouse embryo development in culture. Embryos were cultured from the fertilized egg for 48 h with rHA and HYN in the presence or absence of citrate. Embryos were then transferred to culture medium with or without citrate for a further 48 h. Embryos were cultured at 37° C. in 6% $CO_2$:5% $O_2$:89% $N_2$ in an embryo incubation volume of 10 embryos:20 μl of medium. Embryos were cultured in medium G1.2 for 48 h followed by 48 h of culture in medium G2.2. The results are shown below in Table 7.

TABLE 7

| Treatment | Morula/ Blastocyst (%) | Total Blastocyst (%) | Hatching (% of Total) | Cell Number | ICM Number | TE Number | % ICM/ Total |
|---|---|---|---|---|---|---|---|
| −/− | 53.9 | 45.2 | 13 | 100.4 | 28.9 | 71.5 | 28.4 |
| +/− | 71.3 | 67.3 | 16.8 | 112.6 | 34.9 | 77.7 | 30.7 |
| −/+ | 68.5 | 64.8 | 23.2 | 94.8 | 33.4 | 61.44 | 34.5 |
| +/+ | 72.7 | 62.7 | 18.2 | 100.7 | 30.9 | 69.8 | 30.4 |

*Different superscripts are significantly different, P < 0.05.

As can be seen by the results in Table 7, the addition of citrate significantly increased embryo development.

Example 7

Media G1.2/G2.2 were prepared from concentrated stock solutions as taught in Example 1. rHA was added as a 250 mg/ml stock solution of 200 μl to 9.8 mls of media, fermented HYN was added from a ×100 stock solution of 100 μl to 10 mls of media and citrate was added from a ×100 stock solution of 100 μl to 10 mls of media.

Initial experiments in the cow have investigated replacing albumin purified from blood (Bovine serum albumin, BSA) with either rHA or fermented HYN or rHA together with fermented HYN for the development of fertilized eggs in culture. Fertilized eggs were cultured for 6 to 7 days. Embryos were cultured at 38.5° C. in 6% $CO_2$:5% $O_2$:89% $N_2$ in 500 μl of medium. Embryos were cultured in medium G1.2 for 72 h followed by 72 h of culture in medium G2.2. The results are shown below in Table 8.

TABLE 8

| Treatment | Number of Embryos | Total Blastocyst Day 6 | Total Blastocyst Day 7 |
|---|---|---|---|
| BSA | 592 | 30.9[a] | 36.8 |
| rHA | 583 | 22.1[b] | 38.4 |
| HYN | 549 | 16.9[b] | 30.4 |
| rHA + HYN | 558 | 27.8[a] | 39.1 |

*Different superscripts are significantly different, P < 0.05.

The combination of both rHA with the fermented HYN produced equivalent embryo development in culture of cow embryos as that obtained in the presence of BSA.

Example 8

Media G1.2/G2.2 were prepared from concentrated stock solutions as taught in Example 1. rHA was added as a 250 mg/ml stock solution of 200 μl to 9.8 mls of media, fermented HYN was added from a ×100 stock solution of 100 μl to 10 mls of media and citrate was added from a ×100 stock solution of 100 μl to 10 mls of media.

Subsequent experiments in the cow have investigated replacing albumin purified from blood (Bovine serum albumin, BSA) with rHA with or without citrate for the development of fertilized eggs in culture. Fertilized eggs were cultured for 6 to 7 days. Embryos were cultured at 38.5° C. in 6% $CO_2$:5% $O_2$:89% $N_2$ in 500 μl of medium. Embryos were cultured in medium G1.2 for 72 h followed by 72 h of culture in medium G2.2. The results are shown below in Table 9.

TABLE 9

| Treatment | Total Blastocyst Day 6 | Day 6 Blastocyst Cell Number | Day 6 Blastocyst Inner Cell Mass Cell Number |
|---|---|---|---|
| BSA | 40.2 | 143 ± 6[a] | 46.2 ± 1.9[a] |
| rHA | 36.6 | 123 ± 7[b] | 37.9 ± 1.9[b] |
| rHA + citrate | 41.4 | 146 ± 5[a] | 45.3 ± 1.9[a] |

*Different superscripts are significantly different, P < 0.05.

Supplementing rHA with citrate resulted in equivalent cow embryo development in culture compared to those embryos cultured in the presence of BSA.

Example 9

Media G1.2/G2.2 were prepared from concentrated stock solutions as taught in Example 1. rHA was added as a 250 mg/ml stock solution of 200 μl to 9.8 ml of media, fermented HYN was added from a ×100 stock solution of 100 μl to 10 ml of media and citrate was added from a ×100 stock solution to 10 ml of media.

Subsequent experiments in the cow have investigated addition of fermented HYN to rHA with citrate for the development of fertilized eggs in culture, and subsequent ability to freeze them. Fertilized eggs were cultured for 6 to 7 days. Embryos were cultured at 38.5° C. in 6% $CO_2$:5% $O_2$:89% $N_2$ in 500 μl of medium. Embryos were cultured in medium G1.2 for 72 h, followed by 72 h of culture in medium G2.2. Blastocysts were either stained for cell numbers or frozen and subsequently thawed to assess survival. The results are shown below in Table 10.

TABLE 10

| Treatment | Total Blastocyst Day 7 | Day 7 Blastocyst Cell Number | Survival and Re-expansion Following Freezing |
|---|---|---|---|
| BSA | 42.3 | 150 ± 10 | 38.5[a] |
| rHA + citrate | 50.0 | 134 ± 10 | 57.1[b] |
| rHA + citrate + HYN | 51.1 | 159 ± 10 | 80[c] |

*Different superscripts are significantly different, P < 0.05.

Supplementing medium with rHA, citrate and fermented HYN significantly increased the ability of blastocysts to survive freeing and thawing.

Example 10

Media G1.2/G2.2 were prepared from concentrated stock solutions as taught in Example 1.

This experiment investigated the effects of growing CF1 mouse embryos in culture in the presence of rHA and HYN on the ability of the embryos to survive freezing and thawing. CF1 mouse embryos were cultured to the blastocyst stage and development and ability to survive the freezing procedure was assessed.

TABLE 11

| Treatment | Development to the Blastocyst Stage (%) | Blastocyst Hatching Rates (%) | Re-expansion After Freezing (%) | Hatching After Freezing (%) | Completely Hatched After Freezing |
|---|---|---|---|---|---|
| HSA | 88.2 | 49.0 | 76.1 | 42.9 | 28.6 |
| HSA + HYN | 81.8 | 43.2 | 79.5 | 45.5 | 29.6 |
| rHA + citrate | 85.0 | 53.4 | 77.5 | 57.5* | 40.0* |
| RHA + citrate + HYN | 79.0 | 51.9 | 83.8 | 67.6* | 51.3* |

*Significantly different from HSA, P < 0.05

From these results it can be clearly seen that culture with rHA or rHA with HYN significantly increases blastocyst hatching after thawing compared to blastocysts grown with HSA (P<0.05).

The ability of the blastocysts to outgrow in culture following cryopreservation was also assessed. The outgrowth of both the ICM and TE was scored between 0–3 where 0 represented no outgrowth and 3 represented extensive outgrowth. Outgrowth has been shown to be related to viability (Lane and Gardner, 1997).

TABLE 12

| Treatment | Attachment (%) | Outgrowth of ICM (%) | Outgrowth of TE (%) |
|---|---|---|---|
| HSA | 89.5 | 0.8 ± 0.1 | 1.8 ± 0.1 |
| HSA + HYN | 91.2 | 2.2 ± 0.1* | 1.7 ± 0.1* |
| rHA + citrate | 85.0 | 1.8 ± 0.1* | 1.6 ± 0.1* |
| rHA + citrate + HYN | 86.8 | 2.1 ± 0.1* | 1.9 ± 0.1* |

*Significantly different from HSA, P < 0.05

As can be seen from Table 12, development of the ICM was increased by culturing the embryos in a medium containing rHA or HYN as compared to embryos cultured in human serum albumin.

Example 11

This example illustrates that a medium containing rHA, HYN and citrate allows for the successful expansion of cryopreserved supernumerary blastocysts.

In this example, donated cryopreserved human pronucleate embryos were thawed and cultured in medium G1.3 for 48 hours followed by culturing in medium G2.3, as taught in U.S. patent application Ser. No. 09/201,594 with the following changes. The G1.2–G1.3 media has a $MgSO_4$ concentration from 1.0 to 1.8 and a $CaCl_2$ concentration from 1.8 to 1.0. The changes for the G2.2–G2.3 media are the same as the changes to the G1 media, with the addition on the essential amino acids added at half the concentration and nicotinamide, inositol, and folic acid are not present.

Both media were supplemented with 2.5 mg/ml rHA and 0.125 mg/ml HYN. The freezing solution for the embryos was 4.5% glycerol and 0.1M sucrose (10 min.) followed by 9% glycerol and 0.2M sucrose (7 min.). The embryos were placed in a freezing machine at −6° C., seeded and held for 10 minutes, followed by cooling at 0.5° C. per minute to −32° C. The embryos were then plunged into liquid nitrogen. Immediately post thaw, the embryos were incubated individually in 500 nl of fresh G 2.3 for 4 hours after which they were placed individually in 10 microliters of G 2.3 for overnight culture. All incubations took place in 5% $O_2$:6% $CO_2$:89% $N_2$. The 500 nl samples of media were frozen and analyzed using ultramicrofluorescence. The glucose and pyruvate uptake of the thawed embryos was also measured.

TABLE 13

| Number of Blastocysts | Mean Glucose Uptake (pmol/embryo/h) | Mean Pyruvate Uptake (pmol/embryo/h) | Number of Blastocysts Completely Expanded After 24 h | Number of Blastocysts Completely Hatched After 24 h |
|---|---|---|---|---|
| 16 | 40.6 | 15.2 | 12 (75%) | 5 (31%) |

Example 12

The IVF protocol as outlined in Gardner et al. 1988 and Schoolcraft 1999 were used in this example.

This example demonstrates the advantages of a medium containing rHA, HYN and citrate on the development of human embryos.

TABLE 14

| Treatment Group | Number of Patients | Resulting Pregnancies | Implantation Rates |
|---|---|---|---|
| HSA | 10 | 7 (70%) | 32.8% |
| RHA + citrate + HYN | 12 | 9 (66.7%) | 31.9% |

What is claimed is:

1. A mammalian culture medium supplement comprising recombinant human albumin and fermented hyaluronan, wherein the supplement increases the viability of gametes or embryonic cells cultured in a medium containing the supplement, and further wherein the supplement is free from non-recombinant human albumin.

2. The supplement according to claim 1, further comprising citrate.

3. The supplement according to claim 1, wherein the supplement is free from one or more of non-recombinant macromolecules, non-recombinant human albumin, hyaluronan derived from a warm-blooded vertebrate and combinations thereof.

4. The supplement according to claim 1, wherein the recombinant human albumin is present in a range of about 0.5 mg/ml to about 5.0 mg/ml when added to a medium.

5. The supplement according to claim 1, wherein the fermented hyaluronan is present in a range of about 0.1 mg/ml to about 1.0 mg/ml when added to a medium.

6. The supplement according to claim 2, wherein the citrate is present in a range of about 0.1 mM to about 1.0 mM when added to a medium.

7. The supplement according to claim 1 further comprising a medium that can support embryo or cell development, the medium selected from the group consisting of G1.2/G2.2, KSOM/KSOMaa, M16, SOF/SOFaa, MTF, P1, HTF, Earle's, Hams F-10, M2, Hepes-G1.2, Whitten's and PBS.

8. The supplement according to claim 7, wherein the medium that can support veil development supports embryo development.

9. The supplement according to claim 7, wherein the medium that can support cell development supports mammalian stem cell development.

10. A mammalian culture medium comprising recombinant human albumin, citrate and a medium that can support cell development, wherein the mammalian culture medium increases the viability of gametes or embryonic cells cultured in the mammalian culture medium, and further wherein the mammalian culture medium is free from non-recombinant human albumin.

11. A mammalian culture medium comprising recombinant human albumin, fermented hyaluronan, and a medium that can support cell development, wherein the mammalian vulture medium increases the viability of gametes or embryonic cells cultured in the mammalian culture medium, and further wherein the mammalian culture medium is free from non-recombinant human albumin.

12. A mammalian culture medium comprising recombinant human albumin, citrate, fermented hyaluronan, and medium that em support cell development wherein the mammalian culture medium increases the viability of gametes or embryonic cells cultured in the mammalian culture medium and further wherein, the mammalian culture medium is free from non-recombinant human albumin.

13. The mammalian culture medium according to claim 11, wherein the fermented hyaluronan is present in a range of about 0.1 mg/ml to about 1.0 mg/ml based on the total volume of the mammalian culture medium.

14. The mammalian culture medium according to claim 10, wherein the citrate is present in a range of about 0.1 mM to about 1.0 mM based on the total volume of the mammalian culture medium.

15. A mammalian culture medium comprising recombinant human albumin and a medium that can support cell development, wherein the mammalian culture medium increases the viability of gametes or embryonic cells cultured in the mammalian culture medium and further wherein the mammalian culture medium is free from non-recombinant human albumin, and still further wherein the recombinant human albumin is present in a range of about 0.5 mg/ml to about 5.0 mg/ml based on the total volume of the mammalian culture medium.

16. A mammalian culture medium consisting essentially of:
    (a) a medium that can support mammalian embryo or cell development;
    (b) recombinant human albumin in an amount from about 0.1 mg/ml to about 20.0 mg/ml;
    (c) fermented hyaluronan in an mount from about 0.1 mg/ml to about 5.0 mg/ml; and
    (d) citrate in a concentration from about 0.1 mM to about 5.0 mM,
    wherein the mammalian culture medium increases the viability of gametes or embryonic cells cultured in the medium, and further wherein the mammalian culture medium is free from non-recombinant human albumin.

17. The culture medium according to claim 16, wherein the medium that can support embryo or cell development is selected from the group consisting of G1.2/G2.2, KSOM/KSOMaa, M16, SOF/SOFaa, MTF, P1, HTF, Earle's, Hams F-10, M2, Hepes-G1.2, Whitten's and PBS.

18. The culture medium according to claim 16, wherein the culture medium is free from one or more of non-recombinant macromolecules, non-recombinant human albumin, hyaluronan derived from a warm-blooded vertebrate and combinations thereof.

19. A mammalian culture medium supplement consisting essentially of:

(a) recombinant human albumin in an amount from about 0.125 mg/ml to about 20.0 mg/ml;
(b) fermented hyaluronan in an amount from about 0.1 mg/ml to about 5.0 mg/ml; and
(c) citrate in a concentration from about 0.1 mM to about 5.0 mM, wherein the mammalian culture medium increases the viability of gametes or embryonic cells cultured in the medium, and further wherein the mammalian culture medium is free from non-recombinant human albumin.

* * * * *

UNITED STATES PATENT AND TRADEMARK OFFICE
CERTIFICATE OF CORRECTION

PATENT NO. : 6,762,053 B2
DATED : July 13, 2004
INVENTOR(S) : David K. Gardner and Michelle T. Lane It is certified that error appears in the above-identified patent and that said Letters Patent is hereby corrected as shown below:

Column 1,
Line 25, delete the phrase "the resulting media will contaminated" and replace it with -- the resulting media will be contaminated --.
Line 44, delete the phrase "while at the same eliminating" and replace it with -- while at the same time eliminating --.

Column 4,
Line 32, delete the phrase "The stock solution may added" and replace it with -- The stock solution may be added --.
Line 48, delete the phrase "included within that range limits;" and replace it with -- included within that range limit; --.
Line 50, delete "mg/mil" and replace it with -- mg/ml --.

Column 11,
Line 66, delete the phrase "to survive freeing and thawing." and replace it with -- to survive freezing and thawing. --

Column 14,
Lines 22-23, delete the phrase "werein the mammalian vulture medium increases" and replace it with -- wherein the mammalian culture medium increases --.
Line 30, delete the phrase "that em support cell development" and replace it with -- that can support cell development --.

Signed and Sealed this

Eighth Day of February, 2005

JON W. DUDAS
*Director of the United States Patent and Trademark Office*

UNITED STATES PATENT AND TRADEMARK OFFICE
CERTIFICATE OF CORRECTION

PATENT NO.   : 6,762,053 B2
DATED        : July 13, 2004
INVENTOR(S)  : David K. Gardner and Michelle T. Lane It is certified that error appears in the above-identified patent and that said Letters Patent is hereby corrected as shown below:

Column 14,
Line 2, delete the phrase "can support veil development" and replace it with -- can support cell development --.

Signed and Sealed this

Tenth Day of May, 2005

JON W. DUDAS
*Director of the United States Patent and Trademark Office*